United States Patent [19]
Hastings et al.

[11] Patent Number: 6,099,454
[45] Date of Patent: *Aug. 8, 2000

[54] PERFUSION BALLOON AND RADIOACTIVE WIRE DELIVERY SYSTEM

[75] Inventors: Roger N. Hastings, Maple Grove; Michael J. Urick, Rogers, both of Minn.

[73] Assignee: SciMed Life Systems, Inc., Maple Grove, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/812,248

[22] Filed: Mar. 6, 1997

Related U.S. Application Data

[63] Continuation-in-part of application No. 08/782,471, Jan. 10, 1997, which is a continuation-in-part of application No. 08/608,655, Feb. 29, 1996, Pat. No. 5,882,290.

[51] Int. Cl.[7] .................................................... A61N 5/00

[52] U.S. Cl. ................................................................ 600/3

[58] Field of Search ............................................. 600/1–8

[56] References Cited

U.S. PATENT DOCUMENTS

| | | | |
|---|---|---|---|
| 2,546,761 | 3/1951 | Loftus | 128/1.2 |
| 2,862,108 | 11/1958 | Meilink | 250/106 |
| 2,955,208 | 10/1960 | Stevens | 250/108 |
| 3,060,924 | 10/1962 | Rush | 128/1.2 |
| 3,147,383 | 9/1964 | Prest | 250/108 |
| 3,324,847 | 6/1967 | Zoumboulis | 128/1.2 |
| 3,505,991 | 4/1970 | Hellerstein et al. | 128/1.1 |
| 3,643,096 | 2/1972 | Jeffries, Jr. et al. | 250/108 R |
| 3,669,093 | 6/1972 | Sauerwein et al. | 128/1.1 |
| 3,750,653 | 8/1973 | Simon | 128/1.2 |
| 3,811,426 | 5/1974 | Culver et al. | 128/1.2 |
| 3,861,380 | 1/1975 | Chassagne et al. | 128/1.2 |
| 3,866,050 | 2/1975 | Whitfield | 250/497 |

(List continued on next page.)

FOREIGN PATENT DOCUMENTS

| | | |
|---|---|---|
| 2166915 | 8/1996 | Canada . |
| 0 433 011 B1 | 6/1991 | European Pat. Off. . |
| 0 497 495 A2 | 8/1992 | European Pat. Off. . |

(List continued on next page.)

OTHER PUBLICATIONS

Sutherland, "Managing Cancer Through Synergy", *Administrative Radiology Journal,* Nov. 1996, pp. 21–27.

*Radiotherapy of Intraocular and Orbital Tumors,* Springer–Verlak publisher, Berlin Heidelberg and New York, copyright 1993, pp. 23–30 and 363–367.

Tjho–Heslinga et al., "Results of ruthenium, irradiation of uveal melanoma", *Radiotherapy Oncology,* vol. 29, pp. 33–38, 1993.

Lommatzsch et al., "Radiation effects on the optic nerve observed after brachytherapy of choroidal melanomas with 106Ru/106Rh plaques", *Graefe's Arch. Clin. Exp. Ophthalmology,* vol. 232, pp. 482–487, 1994.

(List continued on next page.)

*Primary Examiner*—John P. Lacyk
*Attorney, Agent, or Firm*—Crompton, Seager & Tufte, LLC.

[57] ABSTRACT

A catheter capable of irradiating blood vessel walls to inhibit restenosis after angioplasty. Catheters are capable of simultaneous irradiation and angioplasty. Preferred catheters include a helical perfusion balloon having closely spaced or contacting adjacent windings when inflated. A helical balloon with strand windings having little space therebetween decreases the amount of blood between the balloon exterior surface and vessel walls. A removable, sheathed, elongate radiation source is used with some embodiments. A fixed, flexible sheath partitioning the catheter lumen into sterile and non-sterile portions is included in another embodiment. Internal rather than external perfusion and use of gas to inflate the balloon decrease the absorption of beta radiation by blood, and liquid inflation fluid, respectively.

17 Claims, 8 Drawing Sheets

U.S. PATENT DOCUMENTS

| | | | |
|---|---|---|---|
| 3,927,325 | 12/1975 | Hungate et al. | 250/435 |
| 4,096,862 | 6/1978 | DeLuca | 128/348 |
| 4,220,864 | 9/1980 | Sauerwein et al. | 250/497 |
| 4,225,790 | 9/1980 | Parsons, Jr. et al. | 250/497 |
| 4,244,357 | 1/1981 | Morrison | 128/1.2 |
| 4,281,252 | 7/1981 | Parsons, Jr. et al. | 250/497 |
| 4,314,157 | 2/1982 | Gaines | 250/497 |
| 4,364,376 | 12/1982 | Bigham | 128/1.1 |
| 4,584,991 | 4/1986 | Tokita et al. | 128/1.1 |
| 4,588,395 | 5/1986 | Lemelson | 604/59 |
| 4,631,415 | 12/1986 | Sauerwein et al. | 250/497.1 |
| 4,702,228 | 10/1987 | Russell, Jr. et al. | 128/1.2 |
| 4,706,652 | 11/1987 | Horowitz | 128/1.2 |
| 4,763,642 | 8/1988 | Horowitz | 128/1.2 |
| 4,763,671 | 8/1988 | Goffinet | 128/786 |
| 4,782,834 | 11/1988 | Maguire et al. | 128/344 |
| 4,784,116 | 11/1988 | Russell, Jr. et al. | 128/1.2 |
| 4,799,479 | 1/1989 | Spears | 128/303.1 |
| 4,815,449 | 3/1989 | Horowitz | 600/7 |
| 4,819,618 | 4/1989 | Liprie | 600/7 |
| 4,851,694 | 7/1989 | Rague et al. | 250/497.1 |
| 4,861,520 | 8/1989 | van't Hooft et al. | 252/644 |
| 4,881,937 | 11/1989 | van't Hooft et al. | 600/3 |
| 4,897,076 | 1/1990 | Puthawala et al. | 600/7 |
| 4,936,823 | 6/1990 | Colvin et al. | 600/7 |
| 4,963,128 | 10/1990 | Daniel et al. | 600/7 |
| 4,969,863 | 11/1990 | van't Hooft et al. | 600/3 |
| 4,976,266 | 12/1990 | Huffman et al. | 128/659 |
| 4,976,680 | 12/1990 | Hayman et al. | 600/7 |
| 4,976,690 | 12/1990 | Solar et al. | 604/96 |
| 5,030,194 | 7/1991 | Van't Hooft | 600/3 |
| 5,032,113 | 7/1991 | Burns | 604/96 |
| 5,059,166 | 10/1991 | Fischell et al. | 600/3 |
| 5,084,001 | 1/1992 | Van't Hooft et al. | 600/3 |
| 5,084,002 | 1/1992 | Liprie | 600/7 |
| 5,092,834 | 3/1992 | Bradshaw et al. | 600/7 |
| 5,103,395 | 4/1992 | Spako et al. | 364/413.26 |
| 5,106,360 | 4/1992 | Ishiwara et al. | 600/2 |
| 5,120,973 | 6/1992 | Rohe et al. | 250/497.1 |
| 5,139,473 | 8/1992 | Bradshaw et al. | 600/3 |
| 5,141,487 | 8/1992 | Liprie | 600/7 |
| 5,147,282 | 9/1992 | Kan | 600/1 |
| 5,163,896 | 11/1992 | Suthanthiran et al. | 600/8 |
| 5,176,617 | 1/1993 | Fischell et al. | 600/3 |
| 5,183,455 | 2/1993 | Hayman et al. | 600/7 |
| 5,199,939 | 4/1993 | Dake et al. | 600/3 |
| 5,213,561 | 5/1993 | Weinstein et al. | 600/7 |
| 5,267,960 | 12/1993 | Hayman et al. | 604/106 |
| 5,282,781 | 2/1994 | Liprie | 600/3 |
| 5,302,168 | 4/1994 | Hess | 600/3 |
| 5,308,356 | 5/1994 | Blackshear, Jr. et al. | 606/194 |
| 5,344,383 | 9/1994 | Liping | 600/3 |
| 5,354,257 | 10/1994 | Roubin et al. | 600/7 |
| 5,370,685 | 12/1994 | Stevens | 623/2 |
| 5,391,139 | 2/1995 | Edmundson | 600/7 |
| 5,405,309 | 4/1995 | Carden, Jr. | 600/3 |
| 5,409,015 | 4/1995 | Palermo | 128/772 |
| 5,411,466 | 5/1995 | Hess | 600/3 |
| 5,417,653 | 5/1995 | Sahota et al. | 604/20 |
| 5,425,720 | 6/1995 | Rogalsky et al. | 604/198 |
| 5,429,582 | 7/1995 | Williams | 600/2 |
| 5,484,384 | 1/1996 | Fearnot | 600/3 |
| 5,498,227 | 3/1996 | Mawad | 600/3 |
| 5,503,613 | 4/1996 | Weinberger | 600/3 |
| 5,503,614 | 4/1996 | Liprie | 600/7 |
| 5,532,122 | 7/1996 | Drukier | 435/5 |
| 5,538,494 | 7/1996 | Matsuda | 600/1 |
| 5,540,659 | 7/1996 | Teirstein | 604/104 |
| 5,545,132 | 8/1996 | Fagan et al. | 604/96 |
| 5,556,389 | 9/1996 | Liprie | 604/264 |
| 5,575,749 | 11/1996 | Liprie | 600/3 |
| 5,605,530 | 2/1997 | Fischell et al. | 600/3 |
| 5,611,767 | 3/1997 | Williams | 600/2 |
| 5,616,114 | 4/1997 | Thornton et al. | 600/3 |
| 5,618,266 | 4/1997 | Liprie | 604/21 |
| 5,624,372 | 4/1997 | Liprie | 600/3 |
| 5,643,171 | 7/1997 | Bradshaw et al. | 600/1 |
| 5,649,924 | 7/1997 | Everett et al. | 606/15 |
| 5,653,683 | 8/1997 | D'Andrea | 604/21 |
| 5,662,580 | 9/1997 | Bradshaw et al. | 600/3 |
| 5,674,177 | 10/1997 | Hehrlein et al. | 600/3 |
| 5,683,345 | 11/1997 | Waksman et al. | 600/3 |
| 5,688,220 | 11/1997 | Verin et al. | 600/1 |
| 5,707,332 | 1/1998 | Weinberger | 600/3 |
| 5,720,717 | 2/1998 | D'Andrea | 604/21 |
| 5,722,984 | 3/1998 | Fischell et al. | 606/198 |
| 5,728,042 | 3/1998 | Schwager | 600/3 |
| 5,730,698 | 3/1998 | Fischell et al. | 600/3 |
| 5,782,740 | 7/1998 | Schneiderman | 600/1 |
| 5,782,742 | 7/1998 | Crocker et al. | 600/3 |
| 5,795,286 | 8/1998 | Fischell et al. | 600/3 |
| 5,800,333 | 9/1998 | Liprie | 600/3 |
| 5,803,895 | 9/1998 | Kronholz et al. | 600/3 |
| 5,807,231 | 9/1998 | Liprie | 600/3 |
| 5,816,259 | 10/1998 | Rose | 128/898 |
| 5,816,999 | 10/1998 | Bischoff et al. | 600/3 |
| 5,820,553 | 10/1998 | Hughes | 600/426 |
| 5,833,593 | 11/1998 | Liprie | 600/3 |
| 5,840,008 | 11/1998 | Klein et al. | 600/3 |
| 5,840,009 | 11/1998 | Fischell et al. | 600/3 |
| 5,840,064 | 11/1998 | Liprie | 604/96 |
| 5,843,163 | 12/1998 | Wall | 623/1 |
| 5,851,171 | 12/1998 | Gasson | 600/3 |
| 5,851,172 | 12/1998 | Bueche et al. | 600/7 |
| 5,855,546 | 1/1999 | Hastings et al. | 600/3 |
| 5,857,956 | 1/1999 | Liprie | 600/7 |
| 5,863,284 | 1/1999 | Klein | 600/3 |
| 5,863,285 | 1/1999 | Coletti | 600/3 |
| 5,865,720 | 2/1999 | Hastings et al. | 600/3 |
| 5,871,436 | 2/1999 | Eury | 600/3 |
| 5,871,437 | 2/1999 | Alt | 600/3 |
| 5,873,811 | 2/1999 | Wang et al. | 600/5 |
| 5,879,282 | 3/1999 | Fischell et al. | 600/3 |
| 5,882,290 | 3/1999 | Kume | 600/3 |
| 5,882,291 | 3/1999 | Bradshaw et al. | 600/3 |
| 5,891,091 | 4/1999 | Teirstein | 604/104 |
| 5,897,573 | 4/1999 | Rosenthal et al. | 606/224 |
| 5,899,882 | 5/1999 | Waksman et al. | 604/96 |

FOREIGN PATENT DOCUMENTS

| | | |
|---|---|---|
| 0 514 913 A2 | 11/1992 | European Pat. Off. . |
| 0 593 136 A1 | 4/1994 | European Pat. Off. . |
| 0 633 041 A1 | 1/1995 | European Pat. Off. . |
| 0 686 342 A1 | 12/1995 | European Pat. Off. . |
| 0 688 580 A1 | 12/1995 | European Pat. Off. . |
| 0 696 906 B1 | 2/1996 | European Pat. Off. . |
| 0 749 764 A1 | 12/1996 | European Pat. Off. . |
| 0 754 472 A2 | 1/1997 | European Pat. Off. . |
| 0 754 473 A2 | 1/1997 | European Pat. Off. . |
| 0 593 136 B1 | 3/1997 | European Pat. Off. . |
| 0 778 051 A1 | 6/1997 | European Pat. Off. . |
| 0 801 961 A2 | 10/1997 | European Pat. Off. . |
| 0 813 894 A2 | 12/1997 | European Pat. Off. . |
| 0 629 380 B1 | 7/1998 | European Pat. Off. . |
| 9102312 | 6/1992 | Germany . |
| 91 02 312 | 8/1992 | Germany . |
| 195 26 680 A1 | 1/1997 | Germany . |
| 197 54 870 A1 | 8/1998 | Germany . |
| 197 24 233 C1 | 12/1998 | Germany . |

| | | |
|---|---|---|
| WO 86/03124 | 6/1986 | WIPO . |
| WO 93/04735 | 3/1993 | WIPO . |
| WO 94/25106 | 11/1994 | WIPO . |
| WO 94/26205 | 11/1994 | WIPO . |
| WO 95/07732 | 3/1995 | WIPO . |
| WO 95/19807 | 7/1995 | WIPO . |
| WO 95/26681 | 10/1995 | WIPO . |
| WO 96/06654 | 3/1996 | WIPO . |
| WO 96/10436 | 4/1996 | WIPO . |
| WO 96/13303 | 5/1996 | WIPO . |
| WO 96/14898 | 5/1996 | WIPO . |
| WO 96/17654 | 6/1996 | WIPO . |
| WO 96/22121 | 7/1996 | WIPO . |
| WO 96/29943 | 10/1996 | WIPO . |
| WO 96/40352 | 12/1996 | WIPO . |
| WO 97/07740 | 3/1997 | WIPO . |
| WO 97/09937 | 3/1997 | WIPO . |
| WO 97/18012 | 5/1997 | WIPO . |
| WO 97/19706 | 6/1997 | WIPO . |
| WO 97/25102 | 7/1997 | WIPO . |
| WO 97/25103 | 7/1997 | WIPO . |
| WO 97/40889 | 11/1997 | WIPO . |
| WO 98/01183 | 1/1998 | WIPO . |
| WO 98/01184 | 1/1998 | WIPO . |
| WO 98/01185 | 1/1998 | WIPO . |
| WO 98/01186 | 1/1998 | WIPO . |
| WO 98/11936 | 3/1998 | WIPO . |
| WO 98/16151 | 4/1998 | WIPO . |
| WO 98/20935 | 5/1998 | WIPO . |
| WO 98/25674 | 6/1998 | WIPO . |
| WO 98/29049 | 7/1998 | WIPO . |
| WO 98/30273 | 7/1998 | WIPO . |
| WO 98/34681 | 8/1998 | WIPO . |
| WO 98/36788 | 8/1998 | WIPO . |
| WO 98/36790 | 8/1998 | WIPO . |
| WO 98/36796 | 8/1998 | WIPO . |
| WO 98/39052 | 9/1998 | WIPO . |
| WO 98/39062 | 9/1998 | WIPO . |
| WO 98/39063 | 9/1998 | WIPO . |
| WO 98/40032 | 9/1998 | WIPO . |
| WO 98/46309 | 10/1998 | WIPO . |
| WO 98/55179 | 12/1998 | WIPO . |
| WO 98/57706 | 12/1998 | WIPO . |
| WO 99/01179 | 1/1999 | WIPO . |
| WO 99/02219 | 1/1999 | WIPO . |
| WO 99/04706 | 2/1999 | WIPO . |
| WO 99/04856 | 2/1999 | WIPO . |
| WO 99/10045 | 3/1999 | WIPO . |

OTHER PUBLICATIONS

Raloff, "Nuclear Medicine Gets Friendlier –Experimental Therapies Seek to Poison Just the Disease", *Science News*, vol. 152, Jul. 19, 1997, pp. 40–41.

Fackelman, "Harbinger of a Heart Attack –Does a Protein in the Blood Foretell Heart Trouble", *Science News*, vol. 151, Jun. 14, 1997, pp. 374–375.

"Aids and Cancer Cured by Hyper–Oxygenation", *Now What*, Issue No. 1, Waves Forest, Monterey, California.

Li et al., "Reactive Oxygen Species Induce Apoptosis of Vascular Smooth Muscle Cell", *FEBS Letters*, 404, 1997, pp. 249–252.

Kalli, "Oxygen Emulsion The Question of Free Radicals", Internet Address http://www.livelinks.com/sumeria/oxy/rad2.html, Aug. 1, 1997.

Barry, "Reactive oxygen Species in Living Systems –Source: Biochemistry, and Role in Human Disease", Internet Address http:/www.livelinks.com/sumeria/oxy/reactive.html, Jul. 21, 1997 from *American Journal of Medicine*, vol. 91, No. 3c, Sep. 30, 1991, p. 14s(9).

Block, "Peroxygen Compounds, Chapter 9", *Disinfection, Sterilization, and Preservation*, Fourth Edition, Lea & Febiger, Philadelphia, Copyright 1991.

Moore, "Free Radial Generation by Thyroid Peroxidase and Its Effects on Cells in Vitro", phD. Dissertation, Group in Endocrinology–University of California, Berkeley, California, Dec. 1990.

PERFUSION BALLOON AND RADIOACTIVE WIRE DELIVERY SYSTEM

CROSS-REFERENCE TO RELATED APPLICATIONS

This application is a continuation-in-part of co-pending U.S. Patent Application Ser. No. 08/782,471, filed Jan. 10, 1997, pending entitled INTRAVASCULAR RADIATION DELIVERY SYSTEM, which is a continuation-in-part of U.S. patent application Ser. No. 08/608,655, filed Feb. 29, 1996, now U.S. Pat. No. 5,882,290 the entire disclosures of which are herein incorporated by reference.

FIELD OF THE INVENTION

The present invention relates generally to intralumenal or intravascular catheters used to delivery radiation inside a living body. More specifically, the present invention relates to radioactive perfusion balloon catheters for therapeutic purposes.

BACKGROUND OF THE INVENTION

Intravascular diseases are commonly treated by relatively non-invasive techniques such as percutaneous transluminal angioplasty (PTA) and percutaneous transluminal coronary angioplasty (PTCA). These therapeutic techniques are well known in the art and typically involve use of a guide wire and a balloon catheter, possibly in combination with other intravascular devices. A typical balloon catheter has an elongate shaft with a balloon attached to its distal end and a manifold attached to the proximal end. In use, the balloon catheter is advanced over the guide wire such that the balloon is positioned adjacent a restriction in a diseased vessel. The balloon is then inflated and the restriction in the vessel is opened.

Vascular restrictions that have been dilated do not always remain open. In approximately 30% of the cases, a restriction reappears over a period of months. The mechanism of this restenosis is not understood. The mechanism is believed to be different from the mechanism that caused the original stenosis. It is believed that rapid proliferation of vascular smooth muscle cells surrounding the dilated region may be involved. Restenosis may be in part a healing response to the dilation, including the formation of scar tissue.

Intravascular radiation, including thermal, light and radio-active radiation, has been proposed as a means to prevent or reduce the effects of restenosis. For example, U.S. Pat. No. 4,799,479 to Spears suggests that heating a dilated restriction may prevent gradual restenosis at the dilation site. In addition, U.S. Pat. No. 5,417,653 to Sahota et al. suggests that delivering relatively low energy light, following dilatation of a stenosis, may inhibit restenosis. Furthermore, U.S. Pat. No. 5,199,939 to Dake et al. suggests that intravascular delivery of radioactive radiation may be used to prevent restenosis. While most clinical studies suggest that thermal radiation and light radiation are not significantly effective in reducing restenosis, some clinical studies have indicated that intravascular delivery of radioactive radiation is a promising solution to the restenosis enigma.

Since radioactive radiation prevents restenosis but will not dilate a stenosis, radiation is preferably administered during or after dilatation. European Patent No. 0 688 580 to Verin discloses a device and method for simultaneously dilating a stenosis and delivering radioactive radiation. In particular, Verin '580 discloses balloon dilatation catheter having an open-ended lumen extending therethrough for the delivery of a radioactive guide wire.

One problem associated with the open-ended lumen design is that bodily fluids (e.g., blood) may come into contact with the radioactive guide wire. This may result in contamination of the bodily fluid and require the resterilization or disposal of the radioactive guide wire. To address these issues, U.S. Pat. No. 5,503,613 to Weinberger et al. proposes the use of a separate closed-ended lumen in a balloon catheter. The closed-ended lumen may be used to deliver a radioactive guide wire without the risk of contaminating the blood and without the need to resterilize or dispose of the radiation source.

The closed-ended lumen design also has draw backs. For example, the addition of a separate delivery lumen tends to increase the overall profile of the catheter. An increase in profile is not desirable because it may reduce flow rate of fluid injections into the guide catheter and it may interfere with navigation in small vessels.

Another problem with both the open-ended and closed-ended devices is that radiation must travel through the fluid filled balloon in order to reach the treatment site. While this is not a problem for gamma radiation, it poses a significant problem for beta radiation which does not penetrate as well as gamma radiation. Beta radiation is considered a good candidate for radiation treatment because it is easy to shield and control exposure. In larger vessels (e.g., 0.5 cm or larger), a fluid filled balloon absorbs a significant amount of beta radiation and severely limits exposure to the treatment site.

Other intravascular treatments, including delivery of radioactive radiation have been proposed as a means to prevent or reduce the effects of restenosis. For example, U.S. Pat. No. 5,199,939 to Dake et al. suggests that intravascular delivery of radiation may inhibit restenosis. Dake et al. suggest delivering radiation within the distal portion of a tubular catheter. Fischell, in the publication EPO 0 593 136 A1, suggests placing a thin wire having a radioactive tip near the site of vessel wall trauma for a limited time to prevent restenosis. Problems exist in attempting to provide uniform radiation exposure using a point or line source. Specifically, as the radiation varies inversely with the square of distance for a point source and inversely with distance for a line source laying off center near one vessel wall may significantly overexpose the nearby wall while underexposing the further away wall. This is especially critical for beta radiation which is absorbed by tissue and blood at a relatively short distance from the source.

Bradshaw, in PCT publication WO 94/25106, proposes using an inflatable balloon to center the radiation source wire tip. In PCT publication WO 96/14898, Bradshaw et al. propose use of centering balloons which allow blood perfusion around the balloon during treatment. U.S. Pat. No. 5,540,659 to Tierstein suggests use of a helical centering balloon, attached to a catheter at points about the radiation source to allow perfusion through the balloon, between the balloon and radiation ribbon source.

Use of continuous centering balloons, having a beta radiation source within, significantly attenuate the beta radiation when filled with inflation fluid and they may also allow the radiation source to "warp" when placed across curved vessel regions, allowing the balloon to bend but having the central radiation source lying in a straight line between the two ends. Segmented centering balloons may improve the warping problem but may also increase beta attenuation by allowing blood to lie or flow between the beta source and vessel walls. Balloons allowing external perfusion in general have the aforementioned beta attenuation problem. What remains to be provided is an improved apparatus and method for delivering uniform radiation to vessel interiors to inhibit restenosis.

SUMMARY OF THE INVENTION

The present invention includes devices and methods for providing radiation to the interior of human body vessels. Preferred devices include a helical, perfusion balloon, having at least one helical strand configured into multiple windings. The helical balloon adjacent windings are closely spaced or in contact when inflated so as to have insubstantial space separating them. The tight spiral windings or closely spaced windings improve centering of the catheter in the curved or tortuous vascular system due to many more balloon segments than lobed designs. The balloon is capable of being inflated with a gas. Using gas to inflate the balloon results in decreased absorption of radiation by the inflated balloon interior. The passage of beta radiation is especially improved by use of a gas rather than a liquid for inflation. Gas allows beta radiation to pass relatively unhindered from beta source to the balloon wall.

In a first embodiment, the catheter device is a "single operator exchange" catheter suitable for use with a removable, preferably sheathed, radiation source. A second embodiment includes an "over the wire" catheter suitable for use with a removable, preferably sheathed, elongate radiation source. Yet another embodiment is a single operator exchange device having a combination use lumen partitioned into sterile and non-sterile portions by a permanent sheath extending within the catheter lumen. A guide wire can be inserted through the sterile portion, and a radiation source can be inserted through the non-sterile portion. Maintaining a non-sterile portion separate from contact with the patient allows for use of non-sterilized or non-sterilizable radiation sources, while abating the risk of injection for the patient. Radiation sources in the sterilized portion can be re-used without sterilization, saving considerable time and expense.

Single operator exchange devices according to the present invention can have a proximal, extended entry lumen. This allows for retracting a guide wire distal portion out of the lumen area used in common by both the guide wire and the radiation source. The extended entry lumen is sufficiently long to allow the guide wire to maintain position within the catheter, when lying within, yet does not interfere with insertion of the radiation source through the length of the catheter.

In use, the above mentioned devices can be used for irradiation only, or for concurrent irradiation and angioplasty. The devices can be advanced over a guide wire, the guide wire retracted, the radiation source inserted, and the balloon inflated. After angioplasty and/or irradiation are complete, the irradiation source can be retracted, the guide wire advanced, and the catheter retracted over the guide wire while maintaining the wire across the treated area.

The present invention also provides a radiation delivery system that permits the use of an open-ended delivery lumen without the risk of blood contamination and without the need to dispose of or resterilize the radiation source. In addition, the present invention provides a radiation delivery system that permits beta radiation to be delivered through a balloon without a significant decrease in radiation exposure to the treatment site, even in large vessels.

One embodiment of the present invention may be described as a catheter having an open-ended lumen, a radiation source disposed in the open-ended lumen of the catheter and a closed-end sheath surrounding the radiation source. The closed-end sheath prevents blood or other fluids from coming into contact with the radiation source so that blood is not contaminated and the radiation source may be reused. The catheter may be a balloon catheter and may include a guide wire disposed in the open-ended lumen of the catheter. The open-ended lumen may be a full-length lumen or a partial-length lumen (e.g., a rapid exchange lumen). Preferably, the lumen is centered in the balloon for uniform radiation delivery. The catheter may also include a blood perfusion lumen under the balloon or around the balloon. The open-ended lumen in the catheter may have a reduced diameter adjacent the distal end of the catheter to prevent the radiation source from exiting the lumen. Alternatively, the closed-end sheath may have a ridge which abuts a corresponding restriction in the open-end lumen of the catheter to prevent the radiation source from exiting the lumen.

Another embodiment of the present invention may be described as a method of delivering radiation to a treatment site inside the vasculature of a patient using the radiation delivery system described above wherein the method includes the steps of (1) inserting the catheter into the vasculature of a patient; (2) inserting the radiation source into the closed-end sheath; (3) inserting the radiation source and the closed-end sheath into the lumen of the catheter such that the radioactive portion is positioned adjacent a treatment site; and (4) exposing the vascular wall to radiation from the radiation source. Alternatively, the sheath may be inserted into the catheter before the radiation source is loaded into the sheath. The method may also include the steps of (5) removing the radiation source from the catheter; and (6) removing the catheter from the patient. The catheter may be inserted into the vasculature over a guide wire and the guide wire may be removed from the catheter prior to exposing the vascular wall to radiation.

Yet another embodiment of the present invention may be described as a method of delivering radiation to a treatment site inside the vasculature of a patient using a gas-filled balloon catheter and a radiation source wherein the method includes the steps of: (1) inserting the catheter into the vasculature such that the balloon is adjacent to a treatment site; (2) inserting the radiation source into the catheter such that the radioactive portion is adjacent to the balloon; (3) inflating the balloon with a liquid or gas; and (4) exposing the treatment site to radiation from the radiation source through the gas in the balloon. The balloon may be inflated prior to or subsequent to inserting the radiation source. Preferably beta radiation is used, but other radioisotopes may be employed.

DETAILED DESCRIPTION OF THE PREFERRED EMBODIMENTS

Figure 1:
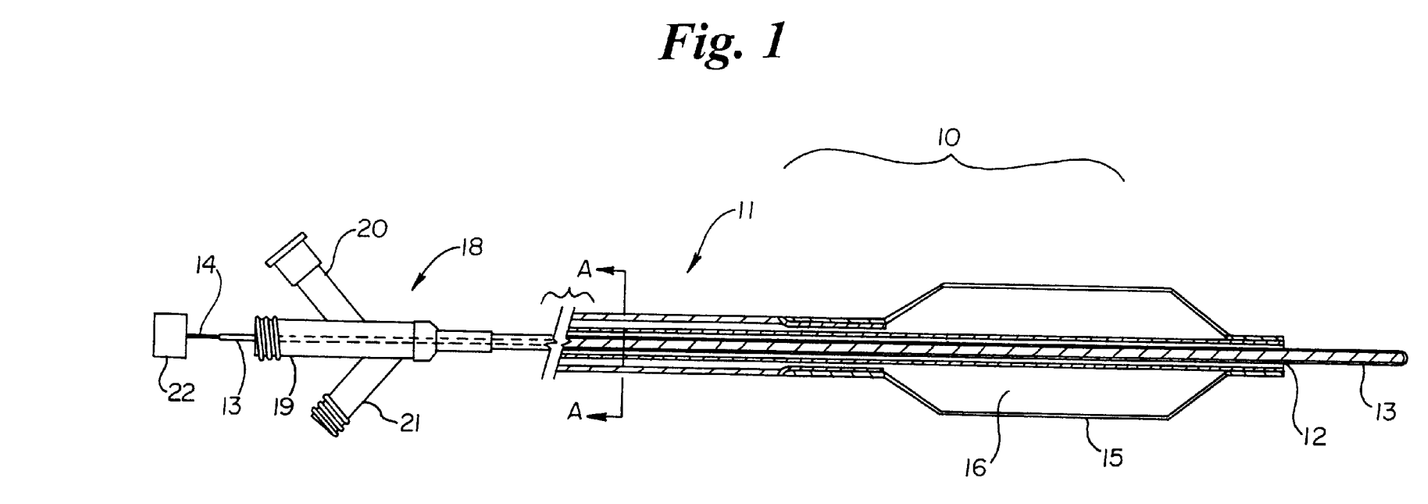
FIG. 1 is a partially sectioned side view of an embodiment of the present invention.
Figure 2:
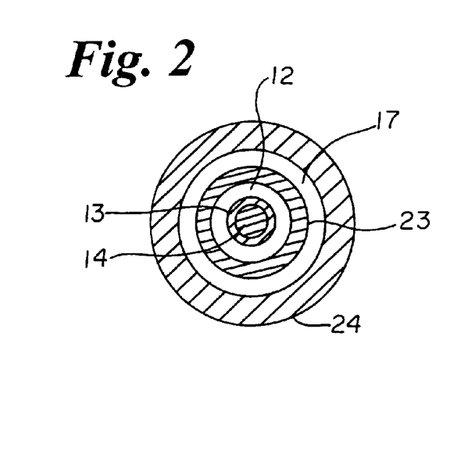
FIG. 2 is a cross-sectional view taken at A—A in FIG. 1.

Refer now to FIGS. 1 and 2 which illustrate one embodiment of a radiation delivery system 10 of the present invention. Radiation delivery system 10 includes a catheter 11 having an open-ended lumen 12 extending therethrough. A closed-ended sheath 13 surrounds a radiation source 14 (such as a guide wire) disposed in the open-ended lumen 12. An after-loader 22 may be connected to the proximal end of the radiation source 14 to advance and retract the radiation source 14 and safely contain it when not in use.

The catheter 11 includes an inflatable balloon 15 having an interior 16 which is in fluid communication with an inflation lumen 17. The catheter 11 illustrated in FIGS. 1 and 2 has a coaxial shaft construction including an inner tube 23 and an outer tube 24. Other shaft constructions may be employed such as a dual lumen shaft design illustrated in FIG. 6. A manifold 18 is connected to the proximal end of the catheter 11 and includes a guide wire port 19 and a flush port 20 both of which are in fluid communication with the open-ended lumen 12. The guide wire port may include a toughy-borst (not shown) to seal about the proximal end of the closed-end sheath 13. The manifold 18 also includes an inflation port 21 which is in fluid communication with the inflation lumen 17 and the interior 16 of the balloon 15.

The closed-end sheath 13 preferably extends to the proximal end of the catheter 11 and may include means for connection to the after-loader 22. The closed-end sheath 13 may be formed of polyethylene, PTFE coated polyimide or other suitable flexible material. The closed-end sheath 13 may have a length of about 100 to 300 cm depending on the length of the catheter 11. A wall thickness between 0.0002 and 0.005 inches is preferred to minimize profile and radiation absorption.

As included with catheter 11 illustrated in FIGS. 1 and 2, the open-ended lumen 12, closed-ended sheath 13, radiation source 14, after loader 22 and toughy-borst are also included with catheters 31, 41, 51 and 61 as illustrated in FIGS. 3, 4, 5 and 6, respectively. In addition, those skilled in the art will appreciate that the various features of each catheter 11, 31, 41, 51 and 61 may be mixed and matched depending on the desired result. For example, the rapid exchange features of catheter 51 may be incorporated into perfusion catheter 61, resulting in a perfusion rapid exchange catheter for the delivery of radiation. As another example, the centering balloon 35 or 45 may be contained inside balloon 15 of catheters 11 and 61 to provide a centering function, even in curved vasculature.

Figure 3:
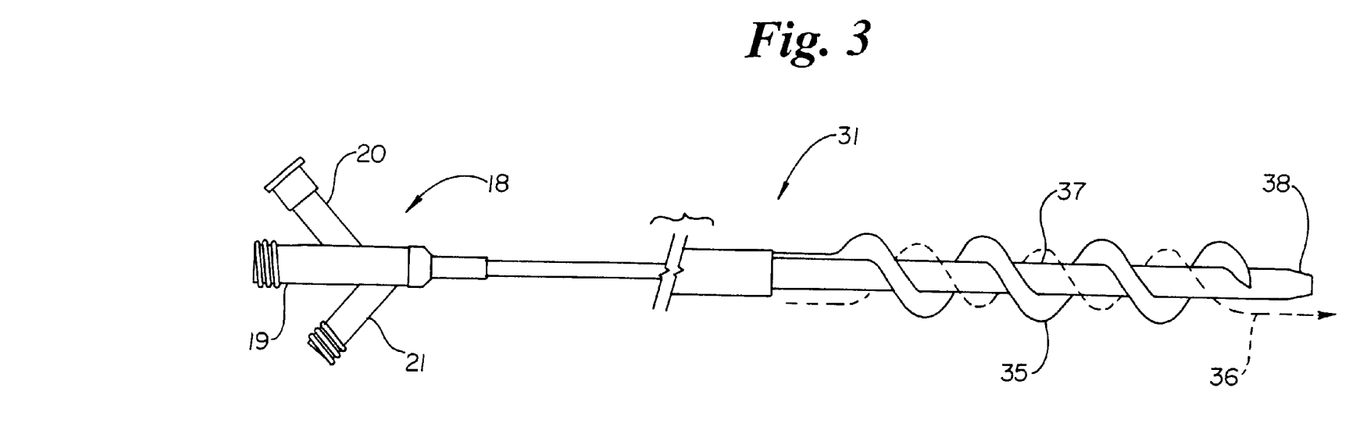
FIG. 3 is a side view of an alternative embodiment of the present invention including a helical-shaped balloon.
Figure 4:
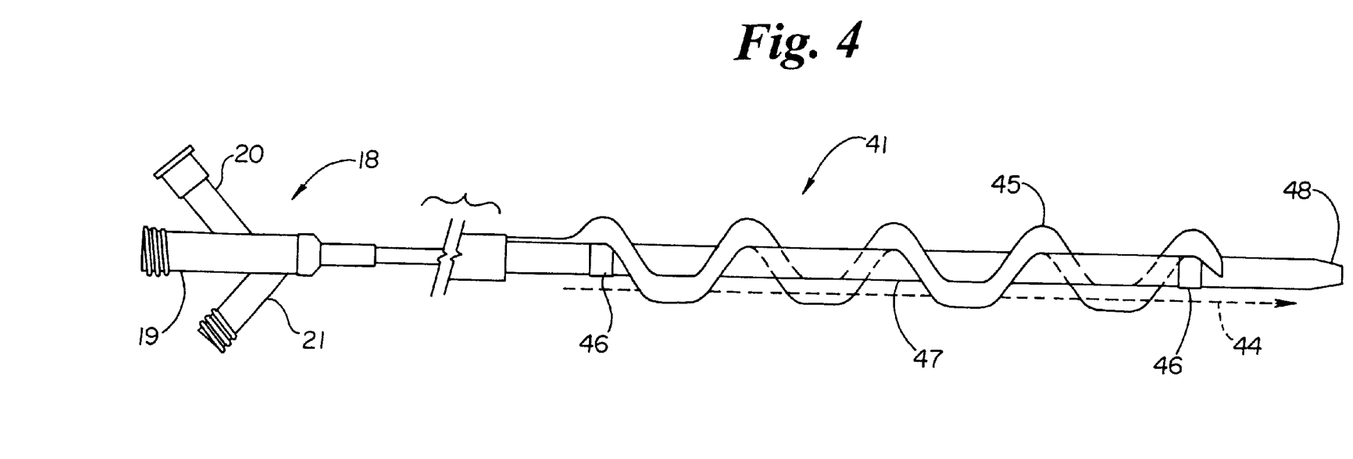
FIG. 4 is a side view of an alternative embodiment of the present invention including a toroidal-serpentine-shaped balloon.

Refer now to FIGS. 3 and 4 which illustrate alternative radiation delivery catheters 31 and 41. Alternative catheters 31 and 41 may be used in place of catheter 11 for the radiation delivery system 10 illustrated in FIG. 1. Except as described herein, the design and use of alternative catheters 31 and 41 is the same as catheter 11. Alternative catheter 41 may be made as described in co-pending U.S. patent application Ser. No. 08/608,655 which is incorporated herein by reference. Similarly, alternative catheter 31 may be made as described in the above-referenced case except that the balloon 35 is wound in a helical shape rather than a serpentine shape.

With reference to FIG. 3, alternative catheter 31 includes a helically-shaped balloon 35 which is wound around the distal end of the catheter 31. When the helically-shaped balloon 35 is inflated, a helically-shaped perfusion path 36 is defined between the balloon 35, the shaft 37 and the inside surface of the blood vessel. The blood perfusion path 36 allows blood to flow across the treatment site while the balloon 35 is inflated. In addition, the concentric and flexible helical shape of the inflated balloon 35 maintains the distal portion of the catheter 31 centered in the vessel, even around turns in the vasculature. Having the catheter 31 centered in a vessel permits the uniform distribution of radiation to the treatment site.

The distal end of the shaft 37 may include a reduced diameter tip 38 with a corresponding reduced inside diameter open-ended lumen (not visible). The reduced inside diameter permits a conventional guide wire to exit out the distal end of the catheter 31 but prohibits the sheath 13 and radioactive source wire 14 from exiting. This assumes, of course, that the sheath 13 or radioactive source wire 14 is larger than the guide wire. A reduced diameter tip may be included on any of the catheters described herein.

With reference to FIG. 4, alternative catheter 41 includes a toroidal-serpentine-shaped balloon 45. When the serpentine-shaped balloon 45 is inflated, a linear perfusion path 44 is defined between the balloon 45, the shaft 47 and the inside surface of the blood vessel. The blood perfusion path 44 allows blood to flow across the treatment site while the balloon 45 is inflated. As with the helical balloon described above, the concentric and flexible serpentine shape of the inflated balloon 45 maintains the distal portion of the catheter 41 centered in the vessel, even around turns in the vasculature. Having the catheter 41 centered in a vessel permits the uniform distribution of radiation to the treatment site. A further advantage of the serpentine-shaped balloon 45 is the relative linearity of the perfusion path 44 which tends to minimize resistance to blood flow.

Catheter 41 may also include two radiopaque markers 46 to facilitate radiographic placement in the vasculature. The distal end of the shaft 47 may include a reduced diameter tip 48 with a corresponding reduced inside diameter open-ended lumen (not visible). The reduced inside diameter permits a conventional guide wire to exit out the distal end of the catheter 41 but prohibits the sheath 13 and radioactive source wire 14 from exiting.

It is also contemplated that both the helical balloon 35 and the serpentine balloon 45 may be covered with an elastomeric sleeve to aid in collapsing the balloon 35/45 upon deflation. This sleeve would be connected to the shaft adjacent the proximal and distal ends of the balloon 35/45. It is further contemplated that this sleeve may include perfusion holes both proximally and distally to permit blood perfusion along the perfusion path 36/44 defined by the balloon 35/45. If a gas is used to inflate the balloon 35/45 in large diameter vessels (e.g., peripheral vasculature), it is preferred to not permit perfusion of blood which would otherwise absorb beta radiation. In such a situation, the sleeve would not include perfusion holes.

Figure 5A:
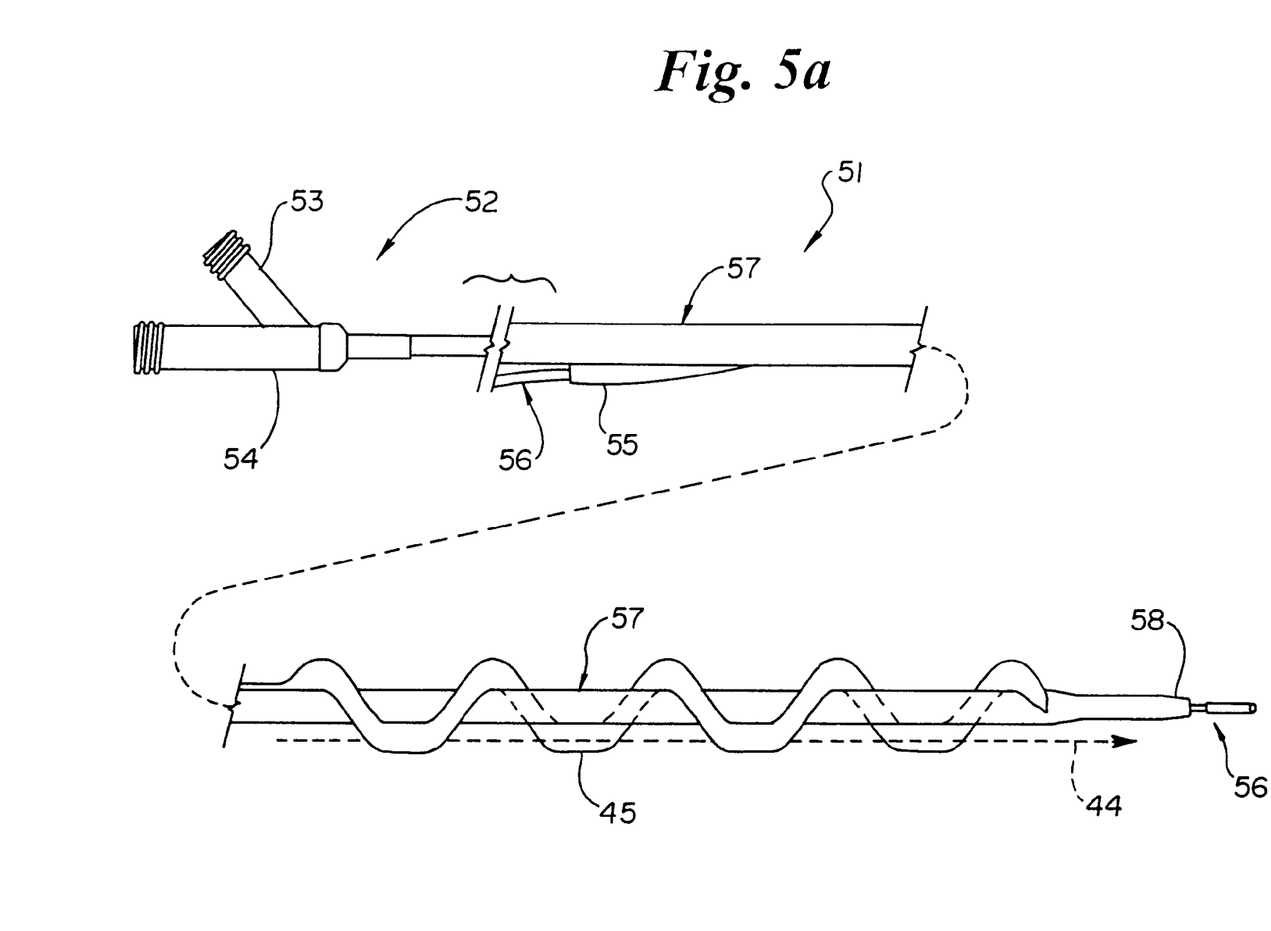
FIGS. 5a, 5b and 5c are partially sectioned side views of an alternative embodiment of the present invention including a rapid-exchange guide wire lumen.
Figure 5B:
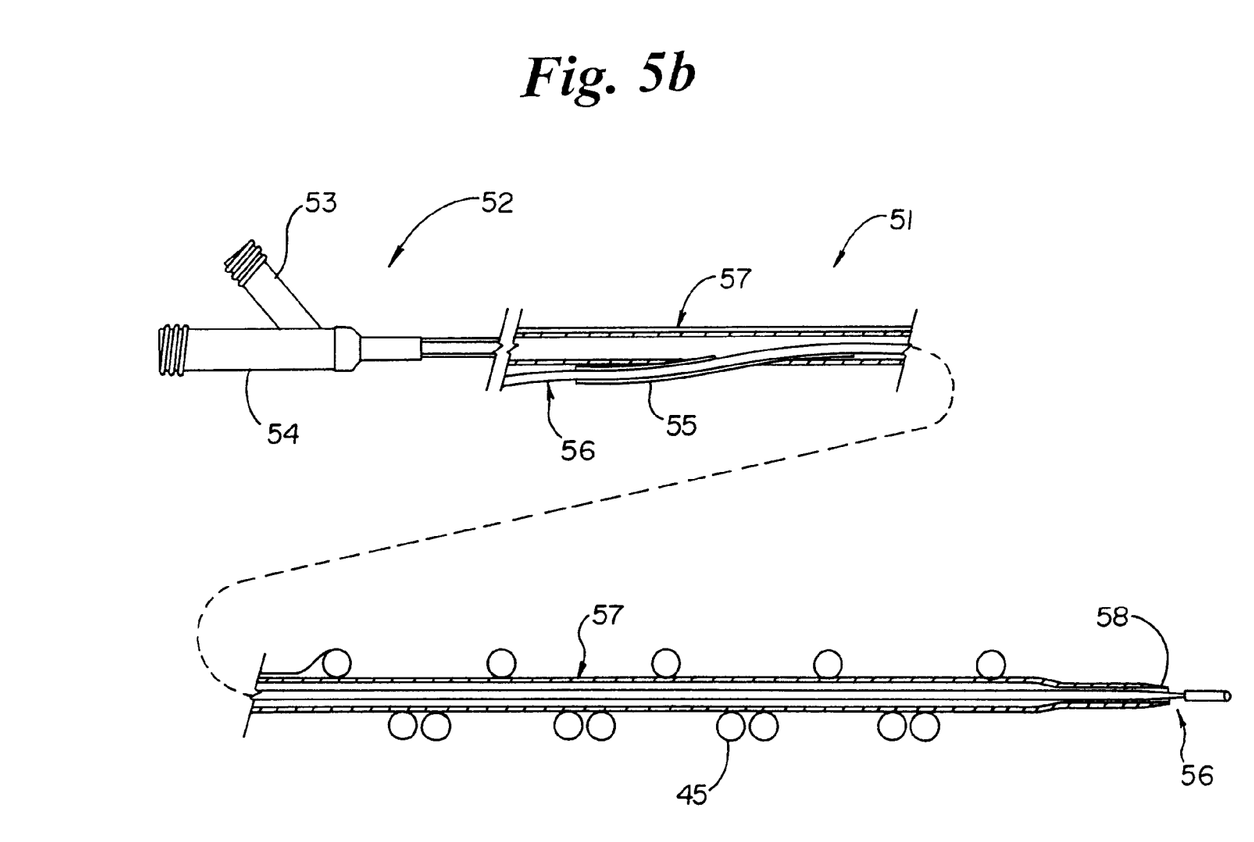
Figure 5C:
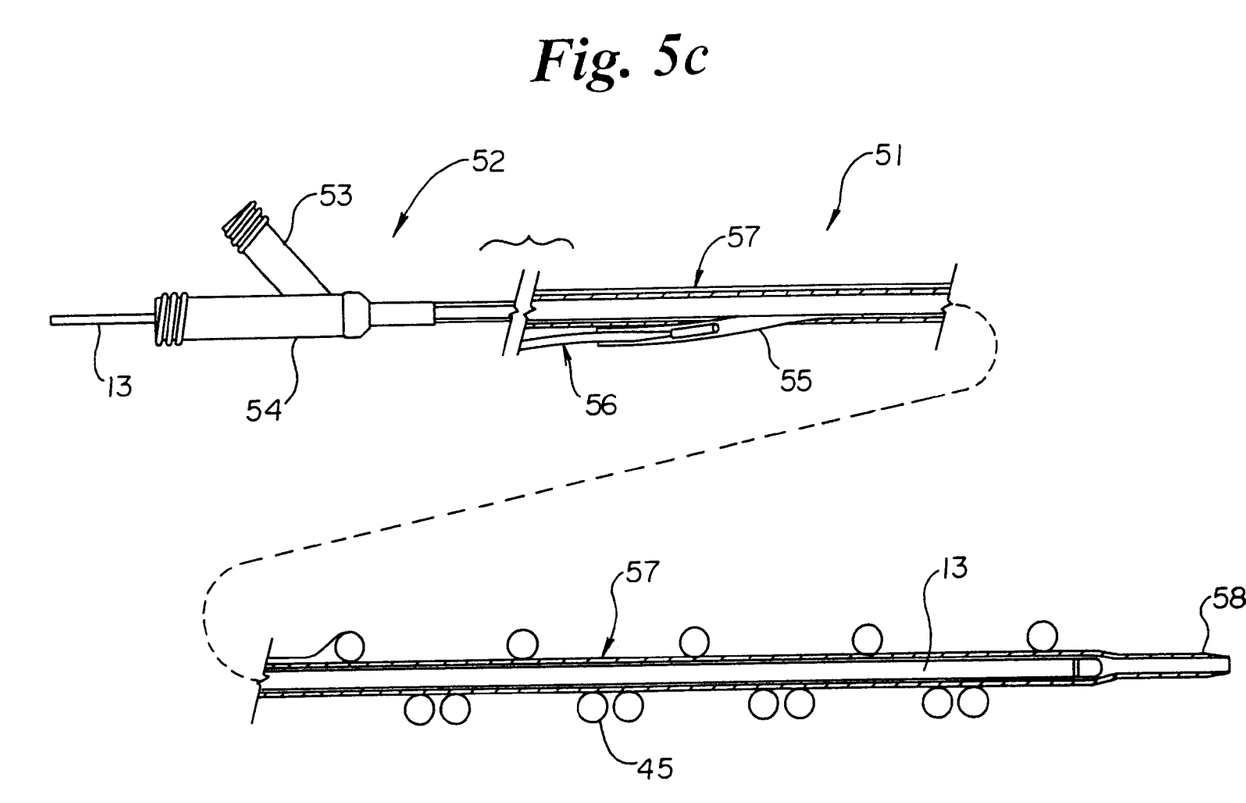

Refer now to FIGS. 5a, 5b and 5c which illustrate a rapid-exchange embodiment of the present invention. Alternative catheter 51 may be used in place of catheter 11 for the radiation delivery system 10 illustrated in FIG. 1. Except as described herein, the design and use of alternative catheter 51 is the same as catheter 11.

Rapid-exchange catheter 51 includes an elongate shaft 57 with a manifold 52 connected to the proximal end and a balloon 45 connected to the distal end. Although catheter 51 is shown with a serpentine balloon 45 and a corresponding linear perfusion path 44, any of the balloon types described herein may be used.

The manifold 52 includes a balloon inflation port 53 which is in fluid communication with the balloon 45 via a conventional inflation lumen. A radiation source entry port 54 is also included in the manifold 52. The entry port 54 communicates with the open-ended lumen and permits the insertion of the sheath 13 and radiation source 14. The open-ended lumen terminates in a reduced diameter tip 58 which permits a conventional guide wire 56 to exit out the distal end of the catheter 51 but prohibits the sheath 13 and radioactive source wire 14 from exiting.

The guide wire 56 enters the shaft 57 at the proximal guide wire tube 55. The guide wire tube 55 is located near the distal end of the catheter to permit catheter exchange without the need for an extension wire or wire trapping device. As best seen in FIG. 5c, the guide wire tube 55 has sufficient length such that the guide wire 56 may be pulled back and out of the open-ended lumen. In particular, the distance from the proximal end of the guide wire tube 55 to the distal end of the catheter 51 is less than the length of the guide wire extending outside of the patient's body. With the guide wire pulled back, the radioactive source wire 14 and the sheath 13 may be inserted into the entry port 54 to the distal end of the catheter 51.

Figure 6:
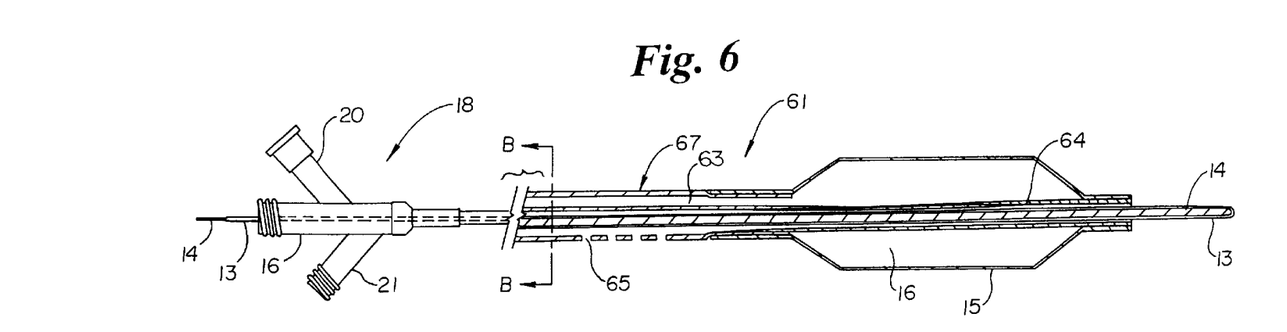
FIG. 6 is a partially sectioned side view of an alternative embodiment of the present invention including a perfusion lumen passing through the balloon.
Figures 7, 8:
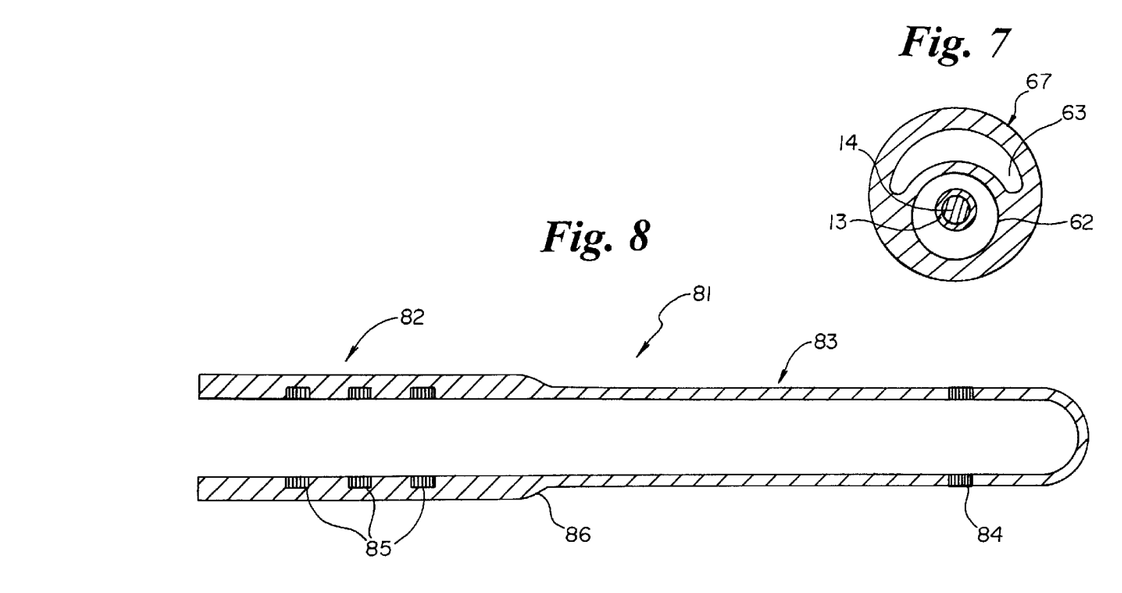
FIG. 7 is a cross-sectional view taken at B—B in FIG. 6.
FIG. 8 is a cross-sectioned side view of an alternative sheath of the present invention.

Refer now to FIGS. 6 and 7 which illustrate an alternative perfusion catheter 61. Alternative catheter 61 may be used in place of catheter 11 for the radiation delivery system 10 illustrated in FIG. 1. Except as described herein, the design and use of alternative catheter 61 is the same as catheter 11.

Perfusion catheter 61 includes an elongate shaft 67 with a manifold 18 connected to the proximal end and a balloon 16 connected to the distal end. The shaft 67 is a multi-lumen type extrusion including an open-ended lumen 62 and an inflation lumen 63. Inflation lumen 63 provides fluid communication between the inflation port 21 and the interior of the balloon 16. Open ended lumen 62 is in communication with entry port 19 for the insertion of a guide wire (not shown) or the radioactive source 14 and sheath 13. A guide wire extension tube 64 is connected to the distal end of the multi-lumen shaft 67 and rigidly connects to the distal end of the balloon 15.

Catheter 61 includes a series of perfusion ports 65 which are in fluid communication with the distal portion of the open-ended lumen 62. The perfusion ports 65 permit blood to flow across the treatment site via the open-ended lumen while the balloon 15 is inflated.

With reference now to FIG. 8, an alternative sheath 81 is illustrated. Alternative sheath 81 may be used in place of sheath 13 for the radiation delivery system 10 illustrated in FIG. 1. Except as described herein, the design and use of alternative sheath 81 is the same as sheath 13.

Sheath 81 includes a proximal portion 82 and a distal portion 83, wherein the proximal portion 82 includes a relatively thicker wall and larger outside diameter. The thicker wall tends to absorb radiation to reduce the amount of unwanted exposure, particularly exposure of the medical personnel. The larger outside diameter of the proximal portion 84 may be used in conjunction with a corresponding restriction in the open-ended lumen 12 of any of the catheters described herein. Specifically, the leading edge or ridge 86 of the proximal portion 82 may abut a mating restriction in the open-ended lumen 12 such that the sheath 81 cannot be advanced beyond that point. The leading edge 86 and the mating restriction in the open-ended lumen serve the same function as the reduced diameter tip described previously and may be used in lieu thereof. In other words, the leading edge 86 and the mating restriction in the open-ended lumen would permit a conventional guide wire 56 to exit out the distal end of the catheter but would prohibit the sheath 81 and radioactive source wire 14 from exiting the distal end of the catheter.

The closed-end sheath 81 may include means for connection to the after-loader 22. The closed-end sheath 81 may be formed of polyethylene, PTFE coated polyimide or other suitable flexible material. The closed-end sheath 81 may have a length of about 100 to 300 cm depending on the length of the catheter 11. On the distal portion 83, a wall thickness between 0.0002 and 0.005 inches is preferred to minimize profile and radiation absorption. On the proximal portion 82, a wall thickness between 0.040 and 1.0 inches is preferred to maximize radiation absorption without significantly compromising profile. The outside diameter of the proximal portion 82 may be greater than the vascular access size on the portion of the sheath 81 that remains outside the body. Once the radiation source is inside the body, the risk of exposure of beta radiation to medical personnel is diminished.

Sheath 81 may also include a radiopaque marker 84 to facilitate radiographic placement of the sheath 81 and radioactive wire 14. Such a radiopaque marker 84 may also be included on sheath 13.

Sheath 81 may also include a series of annular magnets 85. Magnets 85 may be used to interact with a series of magnets connected to the catheter 11, 31, 41, 51 or 61 or a series of magnets connected to a guide catheter (not shown). This general arrangement is described in more detail in PCT publication WO 95/21566 which is fully incorporated herein by reference. The interacting magnets provide a means to longitudinally control and stabilize the position of the radiation source relative to the patient and treatment site.

In practice, catheters 11, 31, 41, 51 and 61 may be used to delivery radiation to the vascular wall in the following manner. After vascular access is established and a guide catheter is in position (if desired), the catheter 11/31/41/51/61 is inserted into the patient with the distal portion adjacent the treatment site. If a guide wire is used, the guide wire may be inserted prior to or simultaneously with the catheter. The balloon is then inflated to a low pressure sufficient to center the balloon in the vasculature and prevent movement of the catheter relative to the treatment site. Optionally, the balloon may first be inflated to a higher pressure in order to dilate the treatment site. If desired, the balloon may be inflated with a gas such as nitrogen, carbon dioxide or other non-toxic gas to minimize the absorption of radiation by the inflation media. After dilatation, the balloon is maintained in an inflated state, preferably at a low pressure, to center the catheter in the vascular lumen. The sheath 13 is placed over the radiation wire 14, preferably ahead of time, and the two are advanced into the open-ended lumen using an after-loader system. Optionally, the sheath 13 is first loaded into the open-ended lumen of the catheter and the proximal end of the sheath is connected to the after-loader, followed by insertion of the radioactive source wire 14. The toughy-borst is maintained sufficiently loose to allow advancement and may be locked to fully seal about the sheath 13 once the radiation wire 14 and sheath 13 are in the desired position. If a guide wire is used in the open-ended lumen, the guide wire is preferably retracted to permit passage of the radioactive wire 14 and sheath 13. If a rapid exchange catheter 51 is used, the guide wire is pulled back into the proximal guide wire tube 55. The vascular wall is then exposed to radiation (preferably beta radiation) for the desired period of time. The radioactive wire 14 and sheath 13 are removed from the catheter 11/31/41/51/61 and the catheter is removed from the patient.

Figure 9:
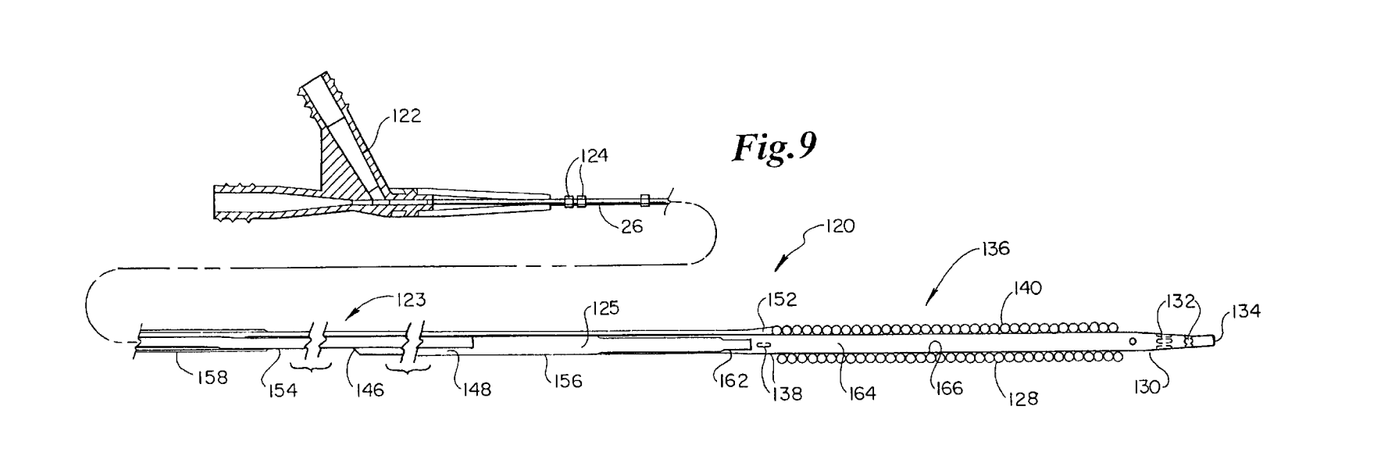
FIG. 9 is a lengthwise, longitudinal cross-sectional view of an single operator exchange catheter according to the present invention.

FIG. 9 illustrates a catheter 120 suitable for single operator exchange according to the present invention. Catheter 120 is illustrated attached to a manifold 122, extending from a proximal portion 126, to a distal portion 128, to a distal end 130. An elongate catheter shaft 123 includes a proximal outer tube 158, an inner tube 154, an intermediate outer tube 156, and a necked inner tube 162. A perfusion head 136 is located near catheter distal portion 128. Perfusion head 136 includes a balloon 140 disposed about a perfusion tube 166 which defines a perfusion lumen 164. Perfusion lumen 164 can transport blood from proximal perfusion ports 138 through to distal perfusion ports 132. A proximal guide wire port 146 and extended entry guide wire lumen 148 allow insertion of a guide wire (not shown) through the catheter and out distal port 134.

Figure 10:
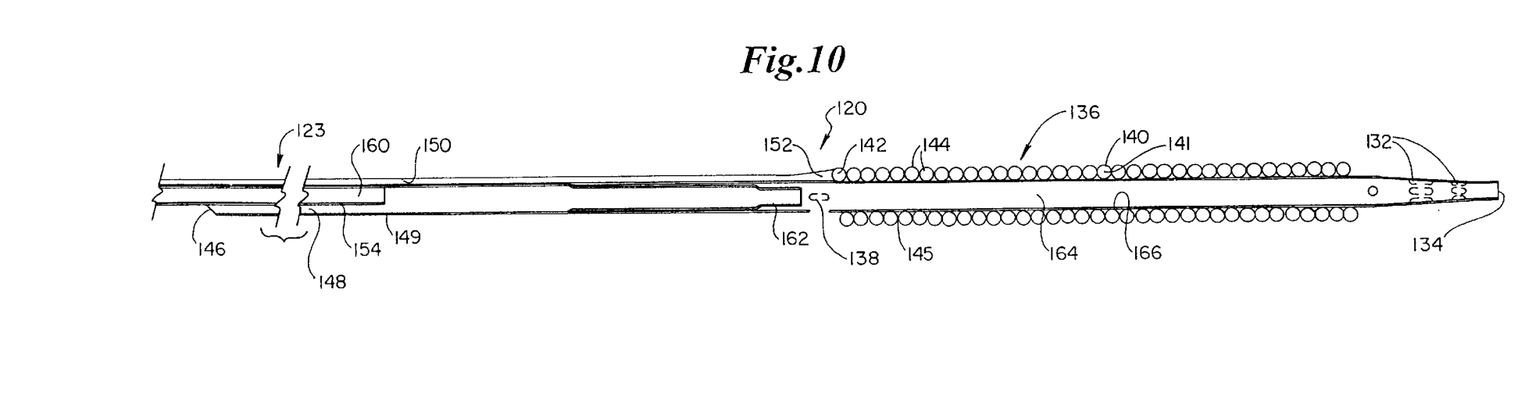
FIG. 10 is an enlarged, lengthwise longitudinal cross-sectional view of a distal portion of the catheter of FIG. 9.

Referring now to FIG. 10, an enlarged view of a proximal portion of catheter 120 is illustrated. Balloon 140 as illustrated, includes a single strand 142 formed into a series of helical windings 144 about perfusion lumen 164. Windings 144 are closely adjacent (preferably in contact when inflated) to each other, having little or no inter-strand spacing, as indicated at 145. An inflation lumen 150, extending proximally from balloon 140, is in fluid communication with the interior of balloon 140, indicated at 141. Helical balloon 140 serves to center perfusion lumen 164, and anything contained within, useful when the balloon is inflated in vessel curves or bends.

In use, a guide wire can be inserted within the vasculature of a patient and advanced to a stenosed site to be treated. Catheter 120 can then have the guide wire proximal end inserted through distal port 134, through the balloon portion, through extended entry lumen 148, and proximally out proximal guide wire port 146. With the guide wire thus threaded, catheter perfusion head 136 can be advanced to the site to be treated. Once in position, a gas under pressure can be used to inflate balloon 140. Either before, during, or after balloon inflation, the guide wire can be partially retracted such that the guide wire distal end is generally near the distal end of extended entry lumen 148, indicated at 149. The length of extended entry lumen 148 is such that the guide wire is able to maintain its position within the extended entry lumen without falling out. The guide wire should not extend distally so far that it interferes with advancement of a radioactive source, discussed below. With the guide wire thus in position, a radioactive source can be advanced from catheter proximal portion 126 through shaft 123 past the distal end of inner tube 154, indicated at 149. A preferred radiation source is a beta emitter, but other radiation sources are contemplated and are within the scope of the invention. One preferred source is Nickel-66. The radioactive source can be advanced further, within perfusion lumen 164 within balloon 140. The radioactive source outside diameter is small enough, and perfusion lumen inside diameter large enough, that sufficient blood is able to perfuse around the radioactive source and through perfusion lumen 164.

With the radiation source thus disposed, the radiation is able to pass relatively unhindered through the gas filled interior 141 of balloon 140 to the surrounding vessel walls. In one method, the pressure is such that concurrent angioplasty and irradiation are carried out. In another method, only irradiation is performed, requiring lower gas pressure. In either of the aforementioned two methods, pressure is supplied sufficient to bring balloon 140 into close contact with the surrounding vessel walls. This excludes substantially all of the blood and external perfusing blood flow from between the balloon exterior and the vessel walls. This removal of interposing blood removes a source of beta radiation attenuation.

Once the radiation exposure period is complete, the radiation source can be withdrawn, and the guide wire can be advanced distally once more. In a preferred method, the radiation source is enclosed in a sheath. This allows for use of a non-sterile radiation source. This allows for use and re-use of a radiation source without requiring either sterilization or disposal of the radiation source. Sterilization or disposal is normally required after use, as the elongate radiation source has been in contact with the patients blood. This contact contaminates the exposed radiation source, requiring either disposal or subsequent sterilization. The sheath can be deployed within the catheter prior to radiation source advancement or slid over the radiation source outside of the catheter, and the sheathed source inserted into the catheter as a unit.

Figure 11:
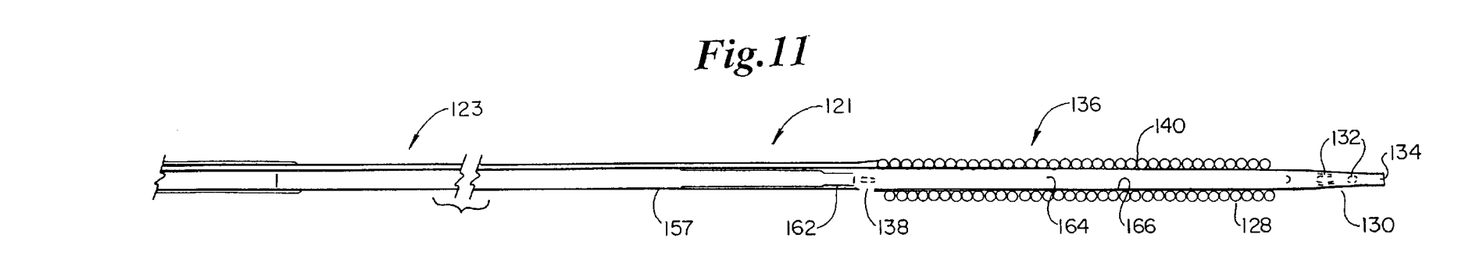
FIG. 11 is a lengthwise, longitudinal cross-sectional view of an over-the-wire catheter according to the present invention.

Referring now to FIG. 11, an "over-the-wire" embodiment of the present invention is illustrated. Catheter 121 is similar in many respects to catheter 120 of FIG. 9, but having an outer tube 157 having no proximal guide wire port suitable for "single operator exchange". Rather, catheter 121 is suitable for use over a guide wire, where the guide wire extends from proximal portion 126 through distal portion 128 and out distal port 134.

In use, a guide wire is positioned near a site to be treated. Catheter 121 can then be advanced over the guide wire, positioning perfusion head 136 near the treatment site. Inflation gas can them be supplied via inflation lumen 150, inflating balloon 140 against the vessel walls. The guide wire can be withdrawn proximally out of the catheter, either before or after balloon inflation. A radioactive source, preferably in a sheath, can then be advanced distally through the catheter, advancement stopping when the radioactive source distal region is disposed within balloon 140.

With the radioactive source disposed within the balloon, radiation treatment can continue for the appropriate time. The advantages of using a sheath, a gas filled balloon, and a tight, helical balloon are described above with respect to the embodiment of FIG. 9. Once treatment is complete, the radiation source can be withdrawn.

Figures 12, 13, 14:
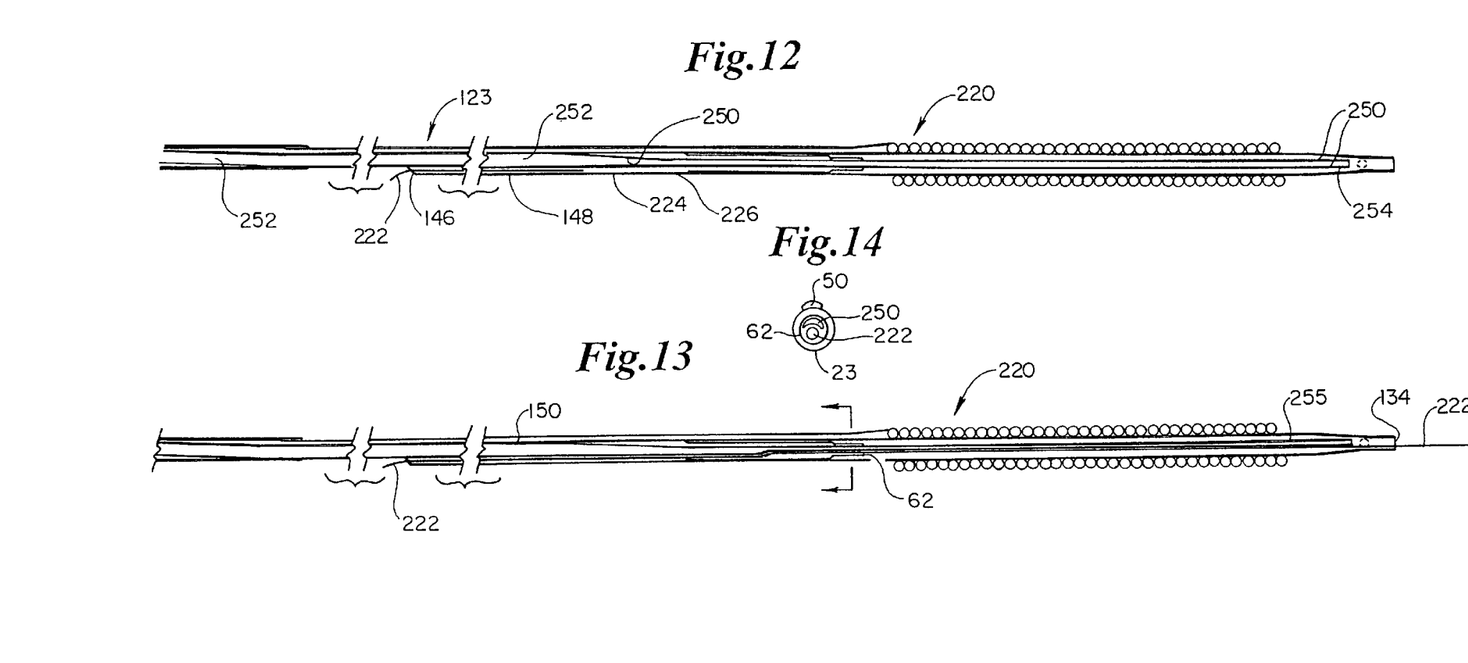
FIG. 12 is a lengthwise, longitudinal cross-sectional view of a single operator exchange catheter having a sheath according to the present invention.
FIG. 13 is a lengthwise, longitudinal cross-sectional view of the catheter of FIG. 12 having a guide wire inserted past the sheath.
FIG. 14 is a cross-sectional view of the catheter of FIG. 13 taken through 14—14.

Referring now to FIG. 12, a "single operator exchange" catheter 220 having a fixed sheath is illustrated. Catheter 220 is similar in many respects to catheter 120 of FIG. 9, with some similar reference numerals omitted for clarity. Catheter 220 includes a sheath 250 within shaft 123, sheath 250 having a proximal portion 252 and a distal portion 254, and is preferably fixed within shaft 123, using a method such as adhesive bonding. A guide wire 222 is illustrated inserted into guide wire proximal entry port 146, lying within extended entry lumen 148. Guide wire 222 has a distal end 226, indicating inserted as far as 224 in FIG. 12.

FIG. 13 illustrates catheter 220 of FIG. 12 having guide wire 222 inserted distally past distal port 134, to necked inner 162. In this configuration, catheter 220 can be advanced or retracted over guide wire 222. Sheath 250 is partially displaced radially by the insertion of the guide wire and does not interfere with guide wire insertion. FIG. 14 illustrates a cross section of catheter 220 taken through 14—14 in FIG. 13, showing that flexible sheath 250 is partially displaced by guide wire 222 being inserted through catheter 220. Both sheath 250 and guide wire 222 are shown within necked inner tube 162. The displacement of sheath 250 is indicated also at 255 in FIG. 13. With guide wire 222 this far inserted, in preferred embodiments, there is insufficient room for insertion of an elongate radioactive source through to perfusion head 136.

Catheter 220 is used in a similar manner to catheter 120 of FIG. 9. Sheath 250 however is displaced by guide wire 222 during catheter advancement and retraction, when the radiation source is withdrawn sufficiently proximally so as to not interfere with guide wire movement within the catheter. Sheath 250 is at least partially filled by an elongate radiation source during radiation exposure of the vessel site. When sheath 250 is containing a radiation source, guide wire 222 is withdrawn sufficiently proximally so as to not interfere with radiation source placement yet lying sufficiently within the extended entry lumen 146 so as maintain guide wire position within the catheter.

Sheath 252 is an illustration of one aspect of the invention, the partitioning of a lumen into sterile and non-sterile portions. In FIG. 12, sheath lumen 252 does not have to be sterile, since it is not in contact with blood. Shaft lumen 125 external to sheath 252 is sterile to prevent patient exposure to infection. This partitioning, accomplished with a flexible partitioning means, allows dual, though not necessarily simultaneous, uses of a lumen. The distal portion of the lumen can be occupied by a disposable guide wire in the sterile portion during catheter advancement or retraction. The distal portion of the lumen can be occupied by a reusable, not necessarily sterile or sterilizable, radiation source once the catheter is in place. The catheter perfusion head 36 profile can thus be kept small by allowing sufficient lumen space for only the guide wire or the radiation source at one time, not both.

Totally enclosing the radiation source in a sheath illustrates one embodiment of the invention. In another embodiment, the lumen is partitioned into sterile and non-sterile portions by dividing the lumen along a longitudinal axis with a flexible wall or membrane, the wall extending across an intermediate portion of the lumen. In this later embodiment, the sterile portion of the lumen is formed in part by a flexible wall and in part by the usually more rigid lumen walls. Furthermore, in one embodiment, this flexible wall need extend longitudinally only from near the guide wire proximal entry port to near the lumen distal end. The remaining proximal portion of the lumen need not be divided by the wall in a single operator exchange embodiment, where there is no need to insert a guide wire.

As previously stated, a preferred source of radiation for all embodiments of the present invention is the radioactive compound Nickel-66. Nickel-66 decays with a half life of 2.28 days with only low energy beta emissions and no gamma emission into its daughter element Copper-66. Copper-66 then emits high energy beta radiation with a half life of 5.10 minutes and decays into the stabile element Zinc-66. This two-step decay has a particular advantage in use in the catheters of the present invention.

The Nickel-66 acts as a carrier for the high energy copper decay allowing for time to transport the source to the end user, and also allows for disposal of the device through ordinary means in about 23 days. A Copper-66 source alone would decay quickly and not be useful without the parent Nickel. Nickel is low cost and has desirable mechanical properties in its pure form and in alloys, such as a Nickel Titanium alloy.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A medical device for insertion within a vessel interior comprising:

a catheter having a longitudinal axis including,
a first elongate member having a proximal portion and a distal portion, said first elongate member having a first lumen therethrough,
means for partitioning said first lumen into a sterile portion and a non-sterile portion, said sterile portion being in fluid communication with said vessel interior, said non-sterile portion segregated from said vessel interior, said means for partitioning being sufficiently flexible to be partially displaced in response to an external elongate member being advanced within either of said sterile or non-sterile portions.

2. A medical device as recited in claim 1, further comprising a second elongate member slidably disposed within said first lumen non-sterile portion.

3. A medical device as recited in claim 1, further comprising a guide wire slidably disposed within said first lumen sterile portion.

4. A medical device as recited in claim 1, further comprising a second elongate member slidably disposed within said first lumen non-sterile portion, wherein said means for partitioning includes a flexible wall, wherein said first lumen has a distal region having an inside diameter sufficient to allow insertion of either a guide wire or said second elongate member, but not both simultaneously.

5. A medical device as recited in claim 4, wherein said second elongate member includes means for therapeutically treating said vessel.

6. A medical device as recited in claim 5, wherein said means for therapeutically treating said vessel is a radiation source and said means for partitioning includes a sheath disposed about said radiation source.

7. A medical device as recited in claim 6, wherein said catheter has a distal portion and a distal end and said first lumen sterile portion has a proximal entry port located in said catheter distal portion proximal of said catheter distal end.

8. A medical device as recited in claim 7, wherein said catheter further comprises an extended proximal entry lumen, said extended proximal entry lumen being in fluid communication with said sterile portion proximal entry port and having a length sufficient to allow a retracted guide wire distal portion to maintain position when lying fully within said extended proximal entry lumen.

9. A medical device as recited in claim 8, further comprising an inflatable balloon disposed about said catheter distal portion, an inflation lumen in fluid communication with said inflatable balloon and a perfusion lumen extending through said balloon.

10. A medical device as recited in claim 9, wherein said inflatable balloon is a helical balloon.

11. A medical device as recited in claim 10, wherein said helical balloon includes at least one helical strand having a strand outside diameter, and said balloon has a longitudinal inter-strand distance, said longitudinal inter-strand distance being substantially less than said strand outside diameter.

12. A medical device as recited in claim 10, wherein said helical balloon includes at least one helical strand configured into a plurality of windings about said longitudinal axis, wherein said balloon has said strand windings adjacent to one another.

13. A method for irradiating a vessel interior at a treatment site comprising the steps of:

providing an elongate radiation source;

providing a catheter including an elongate member having a proximal portion and a distal portion, said member having a first lumen and an inflation lumen therethrough, said catheter including an inflatable balloon disposed near said elongate member distal portion and in fluid communication with said inflation lumen, said first lumen adapted to receive said elongate radiation source and extending longitudinally within said balloon;

inserting said catheter into the vasculature of a patient until said balloon is near said treatment site;

inserting said elongate radiation source into said first lumen distal portion;

inflating said balloon with a gas; and irradiating said treatment site with radiation from said radiation source passing through said gas in said balloon.

14. A method as recited in claim 13, wherein said balloon is a helical balloon having a plurality of adjacent strand windings.

15. A method as recited in claim 14, wherein said catheter includes a guide wire lumen adapted to receive a guide wire and said radiation source is enclosed in an elongate sheath, said method further comprising providing a guide wire and inserting said guide wire near said treatment site, wherein said catheter inserting is performed over said guide wire, and said guide wire is retracted prior to inserting said radiation source.

16. A method as recited in claim 14, wherein said catheter includes a distal portion and a distal end, and said catheter first lumen is partitioned into a sterile portion and a non-sterile portion, said sterile portion being in fluid communication with said vessel interior, said non-sterile portion segregated from said vessel interior, wherein said catheter further comprises an extended proximal entry lumen adapted to receive a guide wire located in said catheter distal portion proximal of said catheter distal end, said extended entry lumen having a proximal port in fluid communication with said vessel interior, said extended entry lumen being distally in fluid communication with said first lumen sterile portion and having a length such that said guide wire is able to maintain position when said guide wire distal portion is retracted from said first lumen sterile portion and extending the length of said extended entry lumen, the method further comprising providing a guide wire having a distal end and inserting said guide wire near said treatment site, wherein said catheter inserting is performed over said guide wire, followed by retracting said guide wire distal end from said first lumen sterile portion and into said extended entry lumen prior to inserting said radiation source, wherein said radiation source is inserted within said first lumen non-sterile portion to a position distal of said guide wire distal end.

17. A method as recited in claim 15, wherein said catheter includes a distal portion and a distal end, wherein said catheter further comprises an extended entry lumen adapted to receive said guide wire located in said catheter distal portion proximal of said catheter distal end, said extended entry lumen having a proximal port in fluid communication with said vessel interior, said extended entry lumen being distally in fluid communication with said first lumen and having a length such that said guide wire is able to maintain position when said guide wire distal end is retracted from said first lumen and said guide wire extends the length of said extended entry lumen, wherein said guide wire distal end remains in said extended entry lumen during said radiation inserting step.

* * * * *